(12) United States Patent
Thornton et al.

(10) Patent No.: US 11,857,455 B2
(45) Date of Patent: *Jan. 2, 2024

(54) REUSABLE DUAL DUROMETER POLYMERIC MENSTRUAL DISCHARGE COLLECTION DEVICE

(71) Applicant: Casco Bay Molding, Sanford, ME (US)

(72) Inventors: Elizabeth Thornton, Scarborough, ME (US); Andrew Powell, Somerville, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/326,852

(22) Filed: May 31, 2023

(65) Prior Publication Data

US 2023/0301821 A1 Sep. 28, 2023

Related U.S. Application Data

(63) Continuation of application No. 18/309,434, filed on Apr. 28, 2023, which is a continuation of application No. 18/059,552, filed on Nov. 29, 2022, which is a continuation of application No. 17/455,555, filed on Nov. 18, 2021, now Pat. No. 11,534,329.

(51) Int. Cl.
*A61F 5/455* (2006.01)
*A61F 5/44* (2006.01)

(52) U.S. Cl.
CPC .......... *A61F 5/4553* (2013.01); *A61F 5/4404* (2013.01)

(58) Field of Classification Search
CPC ...... A61F 5/4553; A61F 5/455; A61F 5/4404; A61F 5/44
See application file for complete search history.

(56) References Cited

U.S. PATENT DOCUMENTS

| | | | | |
|---|---|---|---|---|
| 1,891,761 A | * | 12/1932 | Goodard | A61F 5/4553 604/330 |
| 1,996,242 A | * | 4/1935 | Hagedorn | A61F 5/4553 604/330 |
| 2,089,113 A | * | 8/1937 | Chalmers | A61F 5/4553 D24/141 |
| 2,321,340 A | * | 6/1943 | Waterbury | B29C 70/70 264/294 |
| 2,534,900 A | * | 12/1950 | Chalmers | A61F 5/4553 604/330 |

(Continued)

*Primary Examiner* — Guy K Townsend
(74) *Attorney, Agent, or Firm* — ePatentManager; Guerry L. Grune (57) ABSTRACT

A reusable menstrual discharge collection device is described comprising: dual durometer article that forms a menstrual discharge disc-shaped collection device with a half spherical dome catch where the half spherical dome catch includes a continuous circumferential top and bottom portion, and wherein the continuous top portion is attached to a continuous uniform flexible hinge that is placed along an entire circumferential uniform upper portion of the half spherical dome catch and wherein the hinge also forms a base for and is connected to a 360-degree continuous uniform circumferential rim section such that the hinge allows the half spherical dome catch to be in both an inverted use position/configuration that allows movement of the catch toward the rim section allowing for adjustability to fit multiple cervix physiologies and the elongated configuration allows for ease of manufacturing and cleaning.

16 Claims, 7 Drawing Sheets

(56) References Cited

U.S. PATENT DOCUMENTS

| | | | | |
|---|---|---|---|---|
| 2,616,426 | A | * | 11/1952 | Gordon .................. A61F 5/4553 604/330 |
| 2,836,177 | A | * | 5/1958 | Sells ........................ A61F 6/08 128/837 |
| 3,128,767 | A | * | 4/1964 | Nolan ...................... A61F 6/08 604/330 |
| 3,404,682 | A | * | 10/1968 | Waldron .................. A61F 13/26 128/838 |
| 3,626,942 | A | * | 12/1971 | Waldron .................. A61F 6/08 604/330 |
| 3,841,333 | A | * | 10/1974 | Zalucki .................. A61F 5/4553 604/330 |
| 3,845,766 | A | * | 11/1974 | Zoller .................. A61F 5/4553 D24/141 |
| 4,381,771 | A | * | 5/1983 | Gabbay .................... A61F 6/08 128/836 |
| 4,799,929 | A | * | 1/1989 | Knowles ............... A61F 5/4553 604/331 |
| 4,848,363 | A | * | 7/1989 | Cattanach ............ A61F 5/4553 128/834 |
| 4,961,436 | A | * | 10/1990 | Koch ........................ A61F 6/08 128/834 |
| D323,212 | S | * | 1/1992 | Crawford ...................... D24/141 |
| 5,295,984 | A | * | 3/1994 | Contente .............. A61F 5/4553 604/327 |
| 5,827,248 | A | * | 10/1998 | Crawford .............. A61F 5/4553 604/328 |
| 5,928,249 | A | * | 7/1999 | Saadat .................... A61B 17/42 606/119 |
| 5,947,992 | A | * | 9/1999 | Zadini .................. A61F 5/4553 606/191 |
| 6,126,616 | A | * | 10/2000 | Sanyal ................ A61B 10/0291 128/834 |
| 6,168,609 | B1 | * | 1/2001 | Kamen ................. A61F 5/4553 600/573 |
| 6,241,846 | B1 | * | 6/2001 | Contente .............. B29C 66/114 156/379 |
| 6,264,638 | B1 | * | 7/2001 | Contente ............. A61M 31/002 604/285 |
| 6,332,878 | B1 | * | 12/2001 | Wray ........................ A61F 6/08 128/830 |
| 6,796,973 | B1 | * | 9/2004 | Contente .............. A61F 5/4553 128/832 |
| 7,845,355 | B2 | * | 12/2010 | Moench ..................... A61F 6/08 128/833 |
| 8,454,493 | B2 | * | 6/2013 | La Vean ..................... A61F 6/08 600/33 |
| 8,690,847 | B2 | * | 4/2014 | Norman ............... A61F 5/4553 604/327 |
| 8,795,248 | B2 | * | 8/2014 | Shihata ................ A61F 5/4553 604/385.18 |
| 9,357,982 | B2 | * | 6/2016 | Edmunds ............ A61F 13/2045 |
| 9,827,136 | B2 | * | 11/2017 | Shaviv ....................... A61F 6/08 |
| 10,016,308 | B2 | * | 7/2018 | Knox ................. A61F 13/00085 |
| 10,188,543 | B2 | * | 1/2019 | Lin ....................... A61F 5/4405 |
| D852,361 | S | * | 6/2019 | Sedic ............................. D24/141 |
| D852,362 | S | * | 6/2019 | Sedic ............................. D24/141 |
| 10,357,395 | B2 | * | 7/2019 | Miller ...................... A61F 5/4404 |
| D864,390 | S | * | 10/2019 | Sedic ............................. D24/141 |
| D892,324 | S | * | 8/2020 | Yi ................................. D24/141 |
| D894,386 | S | * | 8/2020 | LeClerc ....................... D24/141 |
| D895,798 | S | * | 9/2020 | Newman ...................... D24/141 |
| D895,799 | S | * | 9/2020 | Newman ...................... D24/141 |
| D895,800 | S | * | 9/2020 | Knox .......................... D24/141 |
| 10,893,975 | B2 | * | 1/2021 | Sedic ........................ A61F 5/4553 |
| 10,898,368 | B2 | * | 1/2021 | Medas ................... A61F 5/4553 |
| 10,959,873 | B2 | * | 3/2021 | Wilson .................. A61F 5/4553 |
| 10,973,496 | B2 | * | 4/2021 | Naseri .................. A61F 13/535 |
| 11,000,402 | B2 | * | 5/2021 | Park ......................... A61F 5/448 |
| 11,013,633 | B2 | * | 5/2021 | Pitacco ................. A61F 5/4553 |
| D923,785 | S | * | 6/2021 | Tsai ............................. D24/141 |
| 11,076,980 | B2 | * | 8/2021 | Hu ........................ A61F 5/4553 |
| 11,154,416 | B2 | * | 10/2021 | Miller ...................... A61F 5/455 |
| 11,234,857 | B2 | | 2/2022 | Miller et al. |
| 11,291,535 | B2 | * | 4/2022 | Conti ................. A61B 10/0012 |
| 11,324,628 | B2 | * | 5/2022 | Bauer .................... A61F 5/4553 |
| 11,464,668 | B2 | | 10/2022 | Lloveras et al. |
| 11,534,329 | B1 | * | 12/2022 | Thornton .............. A61F 5/4404 |
| 2008/0077097 | A1 | * | 3/2008 | Chambers ............. A61F 5/4553 604/330 |
| 2008/0200888 | A1 | * | 8/2008 | Gooch .................. A61F 5/4553 604/330 |
| 2010/0242968 | A1 | * | 9/2010 | Vean ......................... A61F 6/08 128/830 |
| 2010/0312204 | A1 | * | 12/2010 | Sheu ...................... A61F 5/4408 604/330 |
| 2013/0110060 | A1 | * | 5/2013 | Shihata ................. A61F 5/4553 604/330 |
| 2014/0012216 | A1 | * | 1/2014 | Shaviv .................. A61F 5/4553 29/428 |
| 2015/0164680 | A1 | * | 6/2015 | Chen .................... A61F 13/8405 604/359 |
| 2016/0278988 | A1 | * | 9/2016 | Knox ..................... A61F 15/005 |
| 2017/0189222 | A1 | * | 7/2017 | Lin ....................... A61F 5/4553 |
| 2017/0360594 | A1 | * | 12/2017 | Park ........................ A61F 5/449 |
| 2018/0028350 | A1 | * | 2/2018 | Wilson .................. A61F 5/4553 |
| 2018/0199874 | A1 | * | 7/2018 | Hwang ............... A61B 10/0045 |
| 2018/0214298 | A1 | * | 8/2018 | Medas .................. A61F 5/4553 |
| 2019/0021898 | A1 | * | 1/2019 | Ahn ....................... A61F 5/4553 |
| 2019/0083296 | A1 | * | 3/2019 | Miller .................. A61F 5/4553 |
| 2019/0099166 | A1 | * | 4/2019 | Naseri ..................... A61F 13/15 |
| 2019/0125571 | A1 | * | 5/2019 | Hu ........................ A61F 5/4553 |
| 2019/0282350 | A1 | * | 9/2019 | Conti ................. A61B 10/0045 |
| 2019/0314191 | A1 | * | 10/2019 | Bobarikin ............. A61F 5/4553 |
| 2019/0336318 | A1 | * | 11/2019 | Kubo ...................... A61F 5/455 |
| 2019/0358077 | A1 | * | 11/2019 | Bauer .................. A61F 5/4553 |
| 2020/0022835 | A1 | * | 1/2020 | Lloveras Macià .... A61F 5/4553 |
| 2020/0046572 | A1 | * | 2/2020 | Hwang ................. A61F 5/4404 |
| 2020/0078208 | A1 | * | 3/2020 | Stoebe-Latham ..... A61F 5/4553 |
| 2020/0078209 | A1 | * | 3/2020 | Stoebe-Latham ............. A61F 13/55105 |
| 2020/0179157 | A1 | * | 6/2020 | Pitacco ..................... A61F 5/44 |
| 2020/0214876 | A1 | * | 7/2020 | Tsai ...................... A61F 5/4553 |
| 2021/0113363 | A1 | * | 4/2021 | Evans ................... A61F 5/4553 |
| 2021/0128342 | A1 | * | 5/2021 | Miller ...................... A61F 5/455 |
| 2022/0047411 | A1 | * | 2/2022 | Miller ................... A61F 5/4553 |
| 2022/0183812 | A1 | * | 6/2022 | Conti ........................ A61F 2/005 |
| 2023/0149204 | A1 | * | 5/2023 | Thornton .............. A61F 5/4553 604/330 |

\* cited by examiner

REUSABLE DUAL DUROMETER POLYMERIC MENSTRUAL DISCHARGE COLLECTION DEVICE

PRIORITY

This application is a continuation of and claims priority under 35 USC § 120 of U.S. patent application Ser. No. 18/309,434 filed Apr. 28, 2023 entitled "Reusable Dual Durometer Polymeric Menstrual Discharge Collection Device", which is a continuation of Ser. No. 18/059,552 filed Nov. 29, 2022, which is a continuation of Ser. No. 17/455,555 filed Nov. 18, 2021, and granted as U.S. Pat. No. 11,534,329 on Dec. 27, 2022, both entitled "Reusable Menstrual Discharge Collection Device", the entire contents of which are hereby incorporated by reference.

FIELD OF INVENTION

The present disclosure describes a reusable menstrual disc-shaped device produced from either a single contiguous mold, or two molds, consisting of a mold to create the rim and a second mold to overmold the catch onto said rim with the purpose of using different durometer materials for each molding process, thereby providing a single reusable menstruation disc-shaped device or "menstrual disc".

BACKGROUND

The present invention relates generally to feminine hygiene devices, and more particularly to a menstrual discharge collection device for collecting menstrual discharge. From the time after World War I, when bandages were marketed as sanitary napkins, to the present, there have been essentially only two types of commercially available menstrual collection products: sanitary napkins and tampons. Sanitary napkins, including the newer pads and shields, have the disadvantages of bulk, odor, and leakage. They also present disposal problems, and they are sometimes detectable to others. Their absorbent nature can also create problems of contamination and infection. Tampons are also disadvantageous. The basic design of the tampon does not stop leakage and the externally worn string can lead to contamination.

Tampons have fibers which irritate the vaginal mucosa. Absorptive tampons can also contribute to serious infections.

Earlier art describes absorptive cup-shaped vaginal tampons. These devices are bulky and difficult to use and uncomfortable to wear, and would have the same dangers of infection presented by conventional absorptive tampons. Other internal menstrual discharge collection devices are worn in a lower region of the vaginal canal and generate suction, particularly during removal. These devices can cause irritation and pressure, and, in rare cases these devices need to be removed by a doctor.

Further devices have rims with springs embedded therein. Such springs make the devices unnecessarily complicated and expensive to manufacture. The exterior configurations of these devices may also cause irritation when worn internally. Accordingly, there is a need in the art for a menstrual discharge collection device that avoids the problems associated with napkins and tampons, and that is convenient, comfortable, reliable, and economical.

As a result, this device would tend to twist upon compression, making insertion of the device difficult. All of the prior art systems would be difficult to insert and remove, uncomfortable to wear, unreliable, and/or uneconomical to manufacture and market.

Accordingly, there is a need in the art for an intravaginal substance delivery system that can be conveniently and reliably used, and that can be used without discomfort, particularly during menses. In addition the device is reusable and avoids the need for purchasing disposable products such as feminine napkins or other insertable devices that can absorb bodily fluids in or around the area of the vagina.

SUMMARY

The present disclosure describes a single continuous menstruation disc-shaped device designed to collect menstrual fluid during a person's menstrual cycle. The reusable menstruation disc-shaped device is produced from a single contiguous mold or from two molds, consisting of a mold to create the rim and a second mold to overmold the catch onto said rim with the purpose of using different durometer materials for each molding process, thereby providing a single reusable menstruation disc-shaped device or "menstrual disc". The disc-shaped device includes a hinge-enabled invertible half spherical dome catch that when in the elongated position allows for proper cleaning of the menstruation disc-shaped device. In addition, once the menstruation disc-shaped device is inverted during use, the continuous hinge provides a configuration that naturally creates a continuous finger-groove cavity under the rim thus allowing for both ease of retrieval and removal in any rotation.

More specifically, the present disclosure provides for a reusable menstrual discharge collection device, comprising: a continuous single piece article that forms a disc-shaped menstrual discharge collection device with a half spherical dome catch such that the half spherical dome catch includes a continuous top and bottom portion, wherein the continuous top portion is attached to a continuous flexible hinge that is placed along an entire circumferential upper portion of the half spherical dome catch and wherein the hinge also forms a base for and is connected to a 360 degree continuous rim section such that the hinge allows the half spherical dome catch to be in an inverted use position that allows movement of the catch toward the continuous rim section such that the menstrual discharge collection device provides adjustability and ease of extraction with a required flexibility so that the menstrual discharge collection device fits multiple cervix physiologies.

This reusable menstrual discharge collection device includes an elongated configuration that provides for both ease of manufacturing and for cleaning said menstrual discharge collection device after use.

The device is a menstrual disc-shaped device that also functions as a shallow cup.

The device is formed as a single article in a single mold that processes injection molded high temperature resistant thermoplastic rubber.

Alternatively, the device is formed as a single article undergoing two injection molding processes that provide the device by utilizing two separate mold cavities. The first mold cavity forms a relatively firm rim that is designed for a liquid silicon rubber (LSR) or other polymeric material with a Shore A hardness of at least 45. The second mold cavity forms a relatively flexible catch with a continuous flexible hinge using a liquid silicon rubber (LSR) or other polymeric material with a Shore A hardness of 35 or less. Both mold cavities utilize processes that provide injection molded high temperature liquid silicone rubber or other thermoplastic alternatives and/or including thermoplastic elastomers (TPEs) so that a dual durometer device can be achieved.

The half spherical dome catch is collapsible so as to be enclosed within the rim section when the device is in a use position.

The reusable menstrual discharge collection device of wherein the rim section has rounded edges.

The half spherical dome catch is collapsible so that the half spherical dome catch is enclosed within the rim section during use, and wherein the device is folded into a teardrop-like position that provides greater ease of insertion than conventional menstrual discharge collection devices.

Here it is also possible to provide an absorbent and antimicrobial substance that is infused into the half spherical dome catch and more precisely within a bottom portion of the half spherical dome catch, and wherein a distance between the bottom portion of the reservoir and the rim is no less than approximately thirty millimeters when the reservoir is in the device-shaped configuration.

In addition, the rim section is an elastomeric rim section that together with the half spherical dome catch defines a first generally circular configuration for creating a collection space for collecting menstrual discharge, the rim section being compressible from the first configuration to a second generally teardrop-shaped configuration for insertion of the menstrual discharge collection device into position for use, wherein diametrically opposed portions of the rim section are in contact with each other when the rim section is in the second configuration, and wherein the rim section is capable of self-restoring from the second configuration to the first configuration, and wherein the rim section has a height, and a thickness, and wherein the rim section is formed of a high temperature resistant injection molded thermoplastic rubber; and wherein the rim section is formed of liquid silicone rubber.

Often, the device is entirely formed with liquid silicone rubber.

In addition, there are methods of using the menstrual devices described above. One such method includes using a reusable menstrual discharge collection device, comprising:
   providing a continuous single piece article that forms a disc-shaped device with a half spherical dome catch, the half spherical dome catch includes a continuous top and bottom portion, wherein the continuous top portion is attached to a continuous flexible hinge that is placed along an entire circumferential upper portion of the half spherical dome catch and wherein the hinge also forms a base for and is connected to a 360 degree continuous rim section such that the hinge allows the continuous half spherical dome catch to be in an inverted use position that allows movement of the catch section toward the rim section while providing movement and adjustability to fit multiple cervix configurations and an elongated configuration that allows ease of cleaning and manufacturing and;
   wherein the user inserts their fingers while holding a folded teardrop-shaped configuration of the disc-shaped device into their vagina and continue insertion in order to allow pushing the device until the device reaches a fornix of the user and such that a part of the 360-degree continuous rim section of the device is reachable with the user's finger(s) thereby allowing for tucking the device under a pubic bone of the user.

Using this method it is possible to ensure that the menstrual disc shaped device is tucked under the pubic bone the device is in a proper preferred location.

In addition, the menstrual disc shaped device can be folded into a teardrop shape prior to insertion thereby providing a smallest possible shape for easier and more comfortable insertion than has previously been possible.

It is also an object of this disclosure to provide menstruation disc-shaped devices that are produced from a high temperature resistant thermoplastic elastomeric material, for example silicone rubber(s), fluorinated elastomers, and other high temperature resistant polymers capable of withstanding at least 100° C. (for example, the boiling temperature of water). The polymer and/or polymer blend and/or polymer composite, must be able to withstand repeated thermal cycles of boiling liquids (most often water).

Menstrual disc-shaped devices can be created from any safe, acceptable elastomer. Platinum cured medical grade liquid silicone rubber is the preferred material.

In a further embodiment, additional alternative finger loop configurations are also provided. These finger loops can include a circumferential band or stem and loop design.

In another embodiment a polymer is provided (and often an elastomeric thermoset or thermoplastic polymer) that and can withstand at least one repeated usage of boiling water during the sanitization process and in this case the design will often function so that the product can provide at least 365 uses.

DETAILED DESCRIPTION

For the purpose of representing the principles of the disclosure and associated invention, reference will now be made to the drawings and specific language will be used to describe the same. It will nevertheless be understood that no limitation of the scope of the invention is thereby intended, such alterations and further modifications in the illustrated device and such further application of the principles of the invention as illustrated therein being contemplated as would normally occur to one skilled in the art are included as part of the present disclosure.

Figure 1:
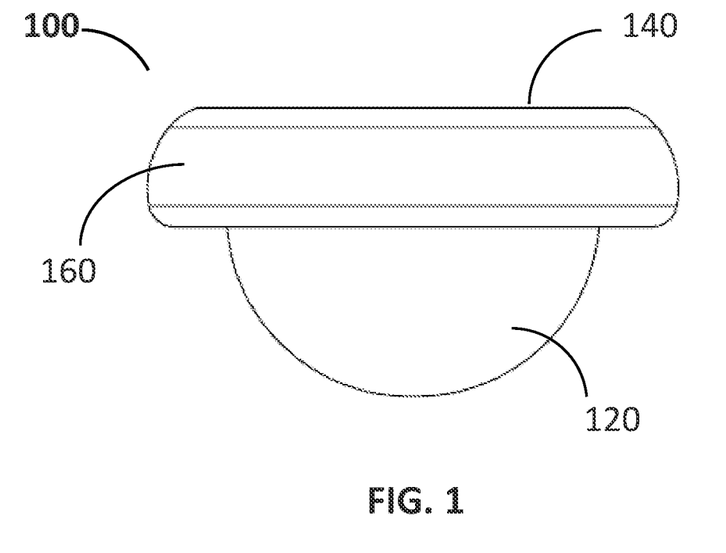
FIG. 1 shows the continuous, single piece article of a menstrual disc-shaped cup in the inverted use configuration.

FIG. 1 shows the continuous, single piece article of a dual durometer polymeric material menstrual disc-shaped device (100) in the inverted "use configuration" comprised of a generally half spherical, thin, flexible, dome shaped catch (120) section that leads to and includes the uniform, continuous, circumferential 360-degree flexible hinge (140) which facilitates the continuous 360-degree continuous rim (160) shown in the dual durometer polymeric material menstrual disc-shaped device (100) use position encompassing the upper parts of the dome shaped catch (120) feature.

Figure 2:
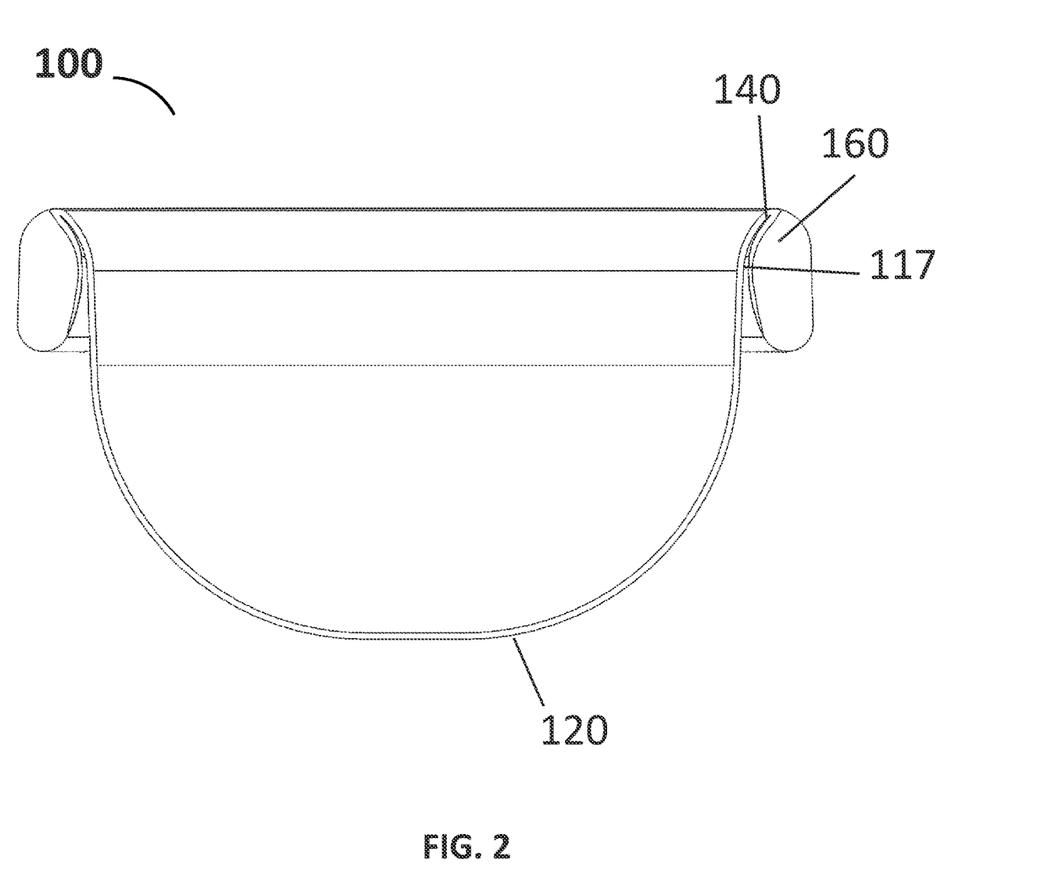
FIG. 2 is a cross sectional view of the menstrual disc-shaped cup in its inverted use configuration with a 360-degree flexible hinge and catch that is comprised of a second material with a different (lower than the second material) durometer hardness such as liquid silicon rubber (LSR) and the uniform circumferential 360-degree continuous rim made from a first material with a higher durometer hardness.

FIG. 2 provides a cross-sectional view of the dual durometer polymeric material menstrual disc-shaped device (100) also shown in its inverted "use configuration". This image more clearly illustrates the domed shaped catch (120) and uniform continuous circumferential 360-degree flexible hinge (140) both, produced from a second polymeric material of lower durometer hardness, attach to the 360-degree continuous rim (160), produced from a first higher durometer polymeric material. The attachment of the continuous 360-degree flexible hinge (140) and 360-degree continuous rim (160) occurs in the "two material bonding area" (117) on the inside diameter of 360-degree continuous rim (160) as shown in this inverted "use configuration". Notably the "two material bonding area" (117) of the 360-degree flexible hinge (140), produced from the second lower durometer polymeric material, does not surround the 360-degree continuous rim (160), produced from the higher durometer hardness first polymeric material. The 360-degree flexible hinge (140) second polymeric material is overmolded onto the 360-degree continuous rim (160) forming a bond on the inside diameter of the 360-degree continuous rim (160). The dual durometer polymeric material menstrual disc-shaped device (100) is comprised of a first polymeric material that is often liquid silicone rubber of a Shore A of 45 or greater, and the second polymeric material often includes a liquid silicone rubber of a Shore A of or less.

Figure 3:
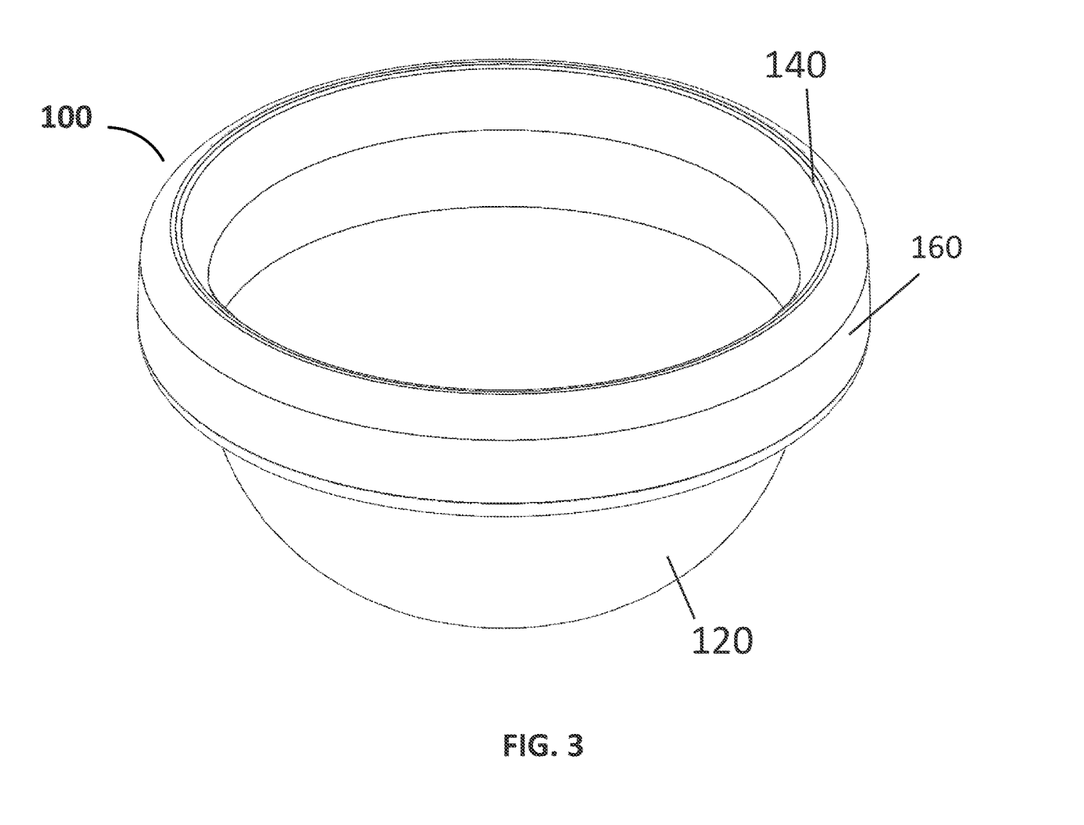
FIG. 3 offers an isometric top view of the menstrual disc-shaped device in its inverted use position revealing a top view of the uniform continuous circumferential 360-degree hinge and 360-degree continuous rim.

FIG. 3 offers an isometric top view of the dual durometer polymeric material menstrual disc-shaped device (100) in its inverted "use configuration" position more clearly revealing a top view of the continuous 360-degree flexible hinge (140) and 360-degree continuous rim (160). This image more clearly illustrates the domed shaped catch (120) and 360-degree flexible hinge (140) both produced from the second polymeric material attached to the circumferential 360-degree continuous rim (160), produced from the first polymeric material. The "two material bonding area" (117) is concealed by the circumferential 360-degree continuous rim (160) in this isometric top view.

Figure 4:
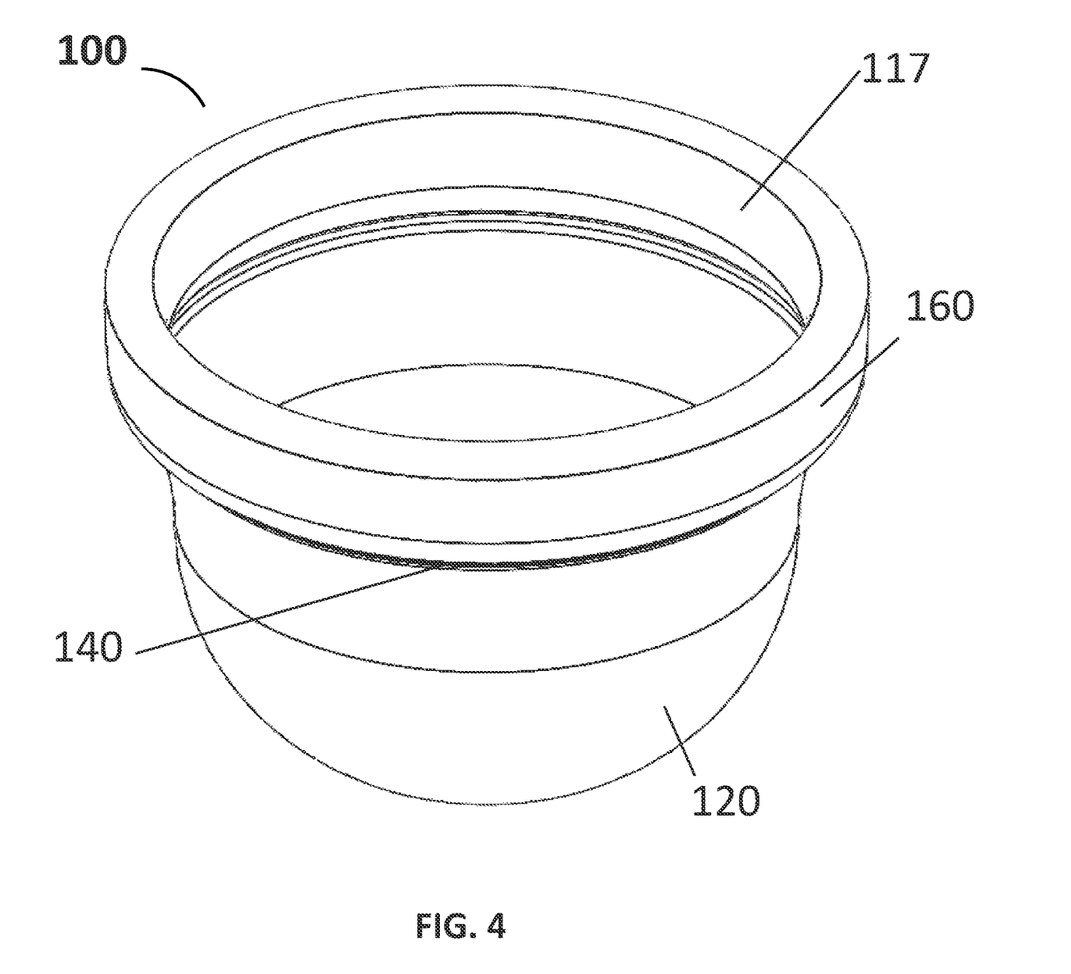
FIG. 4 offers an isometric top view of the menstrual disc-shaped cup in its extended or elongated use configuration that utilizes the 360-degree flexible hinge and catch. The durometer hardness of the hinge and the catch embody the use of different dual durometer hardness polymers. The "two material bonding area" shown is comprised of a thin layer of a second polymer with a lower durometer and more flexible polymer/material overmolded and bonded to the internal diameter of the rim portion comprised of a higher durometer and less flexible first polymer/material.

FIG. 4 is an isometric view of the dual durometer polymeric material menstrual disc-shaped device (100) in its elongated configuration. The thin flexible dome shaped catch (120) and the 360-degree flexible hinge (140), both produced from the second lower durometer polymeric material, connects to the much thicker 360-degree continuous rim (160), produced from the first higher durometer polymeric material when compared with the thinner flexible dome shaped catch (120).

The "two material bonding area" (117) shown on the inside diameter of the 360-degree continuous rim (160), in this elongated configuration isometric view forms the connection and bond between the 360-degree continuous rim (160) and the 360-degree flexible hinge (140) and thinner flexible dome shaped catch (120).

Figure 5:
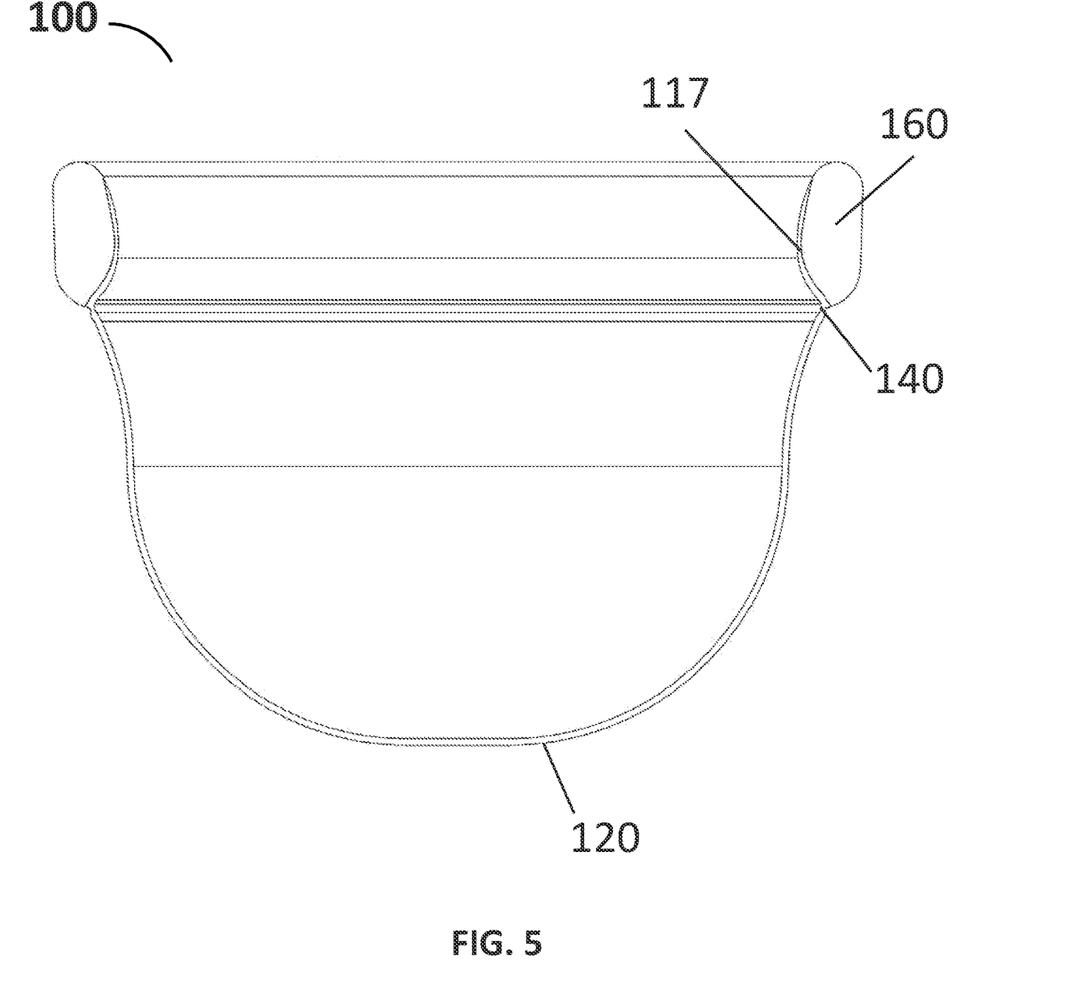
FIG. 5 offers a portion of the cross-sectional view of the menstrual disc-shaped device in its elongated configuration comprised of dual durometer hardness polymers/materials. This illustrates the menstrual disc-shaped device so that the uniform fully continuous circumferential catch and flexible 360 hinge comprised of a second polymer/material are bonded along the interface of the dual durometer hardness polymers. The "two material bonding area" is shown with a thin film of a lower durometer hardness second polymer/material on the inside diameter of the rim comprised of a higher more rigid polymer/material.

FIG. 5 offers a cross sectional view of the dual durometer polymeric material menstrual disc-shaped device (100) in its elongated configuration. The thin flexible dome shaped catch (120) and the 360-degree flexible hinge (140), both produced from the second polymeric material, connects to the much thicker 360-degree continuous rim (160), produced from the first polymeric material when compared with the thinner flexible dome shaped catch (120). More specifically the 360-degree continuous rim (160) is placed into a mold that creates the flexible dome shaped catch (120), 360-degree flexible hinge (140) by overmolding onto the 360-degree continuous rim (160) in the "two material bonding area" (117).

The connection between the 360-degree flexible hinge (140) and 360-degree continuous rim (160) occurs in the "two material bonding area" (117) on the inside diameter of the 360-degree continuous rim (160) as shown in this elongated configuration. Notably the "two material bonding area" (117) of the 360-degree flexible hinge (140), produced from second polymeric material does not fully surround the 360-degree continuous rim (160). More specifically the second polymeric material creates both a flexible dome shaped catch (120) and the 360-degree flexible hinge (140) that partially travels up into the inside diameter portion of the 360-degree continuous rim (160) to create the "two material bonding area" (117). In this manner there is no need for full circumferential bonding to complete the overall dual durometer polymeric material menstrual disc-shaped device (100) design. The dual durometer polymeric material menstrual disc-shaped device (100) is comprised of a first polymeric material, that often utilizes liquid silicone rubber of a Shore A in a range from 45 to 75, and a second polymeric material with a liquid silicone rubber in a Shore A range of from 5 to 35.

The disc-shaped menstrual cup device comprises at least three (3) major features offered in one complete, continuous menstruation disc-shaped device. These at least four features include; a catch, hinge, and a rim. These three featured elements are further described below:

1) The catch provided is a thin-walled, flexible, pliable section of the device that provides a comfortable, dome-shaped element which functions as a device to catch and store menstrual fluid.

2) The hinge connects with the catch to provide a "built-in" living hinge arrangement which allows the thin flexible catch to invert under the rim. The hinge provides an ability to manufacture the rim such that elongation of the menstrual disc design and applied configuration eliminates the possibility of troublesome undercuts to facilitate ease of manufacturing.

The "living" hinge enables the catch to be inverted into a more conventional "use" or "usable" configuration. As the menstrual disc-shaped device is placed in an "inverted catch" or "in use configuration" or position, the menstrual disc-shaped device can be effectively positioned under the cervix. This "living" hinge also allows the user/menstruator to flip the catch back up, into the elongated configuration, for ease of cleaning, after removal and draining. This hinge feature enables the user to easily clean the menstrual disc-shaped device by allowing for exposure of all surfaces to running water and/or boiling water during washing cycles to assure proper sanitation. These washing cycles can be performed automatically in an automatic dishwasher.

3) The rim is optimized in order to provide the radial tear and tensile strength necessary so that the device can open easily and safely once the device is located beneath the cervix. The rim is designed to provide the necessary flexibility by ensuring proper flexural strength so that the device can be pinched by the user into a teardrop shape for easy vaginal insertion and location. This procedure is known as "folding". The 360-degree rim and associated geometry offers a major advantage over conventional designs for ease of removal. Other menstrual disc-shaped devices rotate while in use. The menstrual disc-shaped device without a complete 360-degree rim and hinge which in the inverted use configuration creates a place for the user's finger to naturally grip under the rim in any rotation of the disc can be difficult to grip and extract.

The "use configuration" provides a menstruation disc-shaped device that includes the catch in a "flipped" or inverted position that is directed toward the rim, allowing the menstrual disc-shaped device to be inserted for use and creates a place for the user's finger to naturally grip under the rim in any rotation of the disc for removal.

FIGS. 2 and 5 depict an embodiment of the menstrual disc-shaped device with a rim produced from a firm first material bonded to a more flexible-higher elongation second material that comprises a 360-degree flexible hinge and catch elements. The high elongation hinge and catch aid the menstruator by making the rim easier to grip therefore making it easier to extract the menstrual disc-shaped device. More easily maneuverable and simultaneously minimizes user discomfort due to the firmer rim securing the device and the more flexible, invertible catch and hinge.

The uniform continuous circumferential 360-degree flexible hinge provides the ability to easily invert the catch but also facilitates the user in positioning the device to their needs. By creating an enhanced gap between the rim and the hinge with a more flexible softer durometer catch the user has access to more easily provide proper positioning and or removal of the device.

In an additional embodiment, alternate configurations of the rim can be manufactured to provide indentions, protrusions and/or "through-orifices" in order to allow the user to more easily grip the disc-shaped device for insertion, repositioning, or removal. Inverting the catch configures the disc to provide a flexible, softer part of the disc so that the disc can be positioned in a more proximate location to the cervical area.

4) Previous designs provided tethers attached on the outside of the rim, which greatly increased the chance of the tether irritating the menstruator.

Menstruators are people that come in all shapes and sizes, with different cervix heights and preferred menstrual device or disc-like geometries. The dual durometer polymeric material menstrual disc-shaped device described herein can be modified for different diameters and catch configurations to meet the needs for different users.

The most common method of manufacturing the menstrual disc-shaped device is by injection, transfer, or compression molding which enables the menstrual disc-shaped device to be molded in an elongated "wind-sock" shaped design followed by removal and subsequent inversion to create the final rim detail.

Thermoplastics and Liquid Silicone Rubber (LSR) plastics are either organic or semi-organic (if inorganic fillers or inorganic monomers and polymers are used) materials that have (as their main attribute) relatively high tensile strength, elongation at break and tear strength due to their high molecular weights. Most engineers and manufacturers consider LSRs as thermosets in that they normally cannot be reused to make the same product. Alternatively, thermoplastics often allow the use of regrind during molding and extrusion operations. For the present disclosure the menstrual disc-shaped device is produced using one or more polymers that may include any of moldable thermosets, thermoplastics and/or elastomers. The list of possibilities includes thousands of variations of these polymers which includes polymer blends, composites, dual layered polymer systems, and also a large number of possible fillers to complete the product.

Smooth surfaces and transitions of the menstrual disc-shaped device are required to minimize the potential for irritation, facilitate cleaning, and ease of manufacturability.

The boiling water can be heated with one or more heating devices selected from the group consisting of ovens, stovetops, microwaves, wood-burning or other energy sourced stoves, infrared burners, sonic containers, and solar devices. In some cases, dishwashers and/or autoclaves can be used for cleaning and sanitizing purposes.

Working Example

Figure 6:
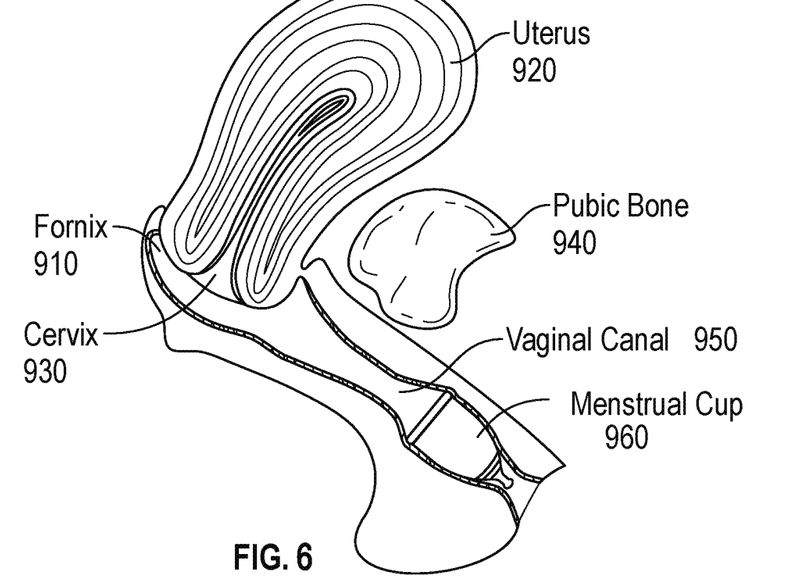
FIG. 6 provides a cross-sectional view of the location and position of the menstrual cup shaped device in the uterine canal to show the difference between cup and disc locations.
Figure 7:
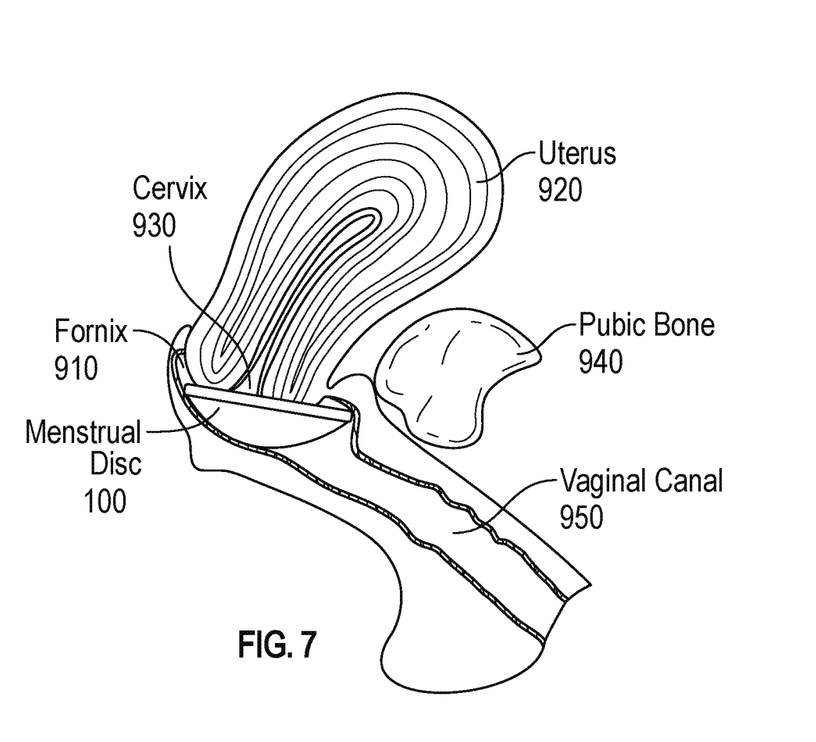
FIG. 7 illustrates a cross-sectional view of the position of the menstrual disc as it relates to the cervix and fornix to show the difference between cup and disc locations.

FIGS. 6 and 7 demonstrate how the devices of the present disclosure are utilized in practice. FIG. 6 shows that both the menstrual cup (960) and dual durometer polymeric material menstrual disc-shaped device (100) collect menstrual fluids and can be worn for up to 12 hours, however their location and use varies slightly.

As shown in FIG. 6, the menstrual cup (960) is located/placed lower in the vaginal canal (950) usually within an inch of the opening of the vagina and away from the fornix (910) and cervix (930). The menstrual cup (960) does not tuck behind the pubic bone (940). It uses the muscular structure of the vaginal walls to create a seal and prevent leaks.

FIG. 7 reveals the dual durometer polymeric material menstrual disc-shaped device (100) positioned higher up in the vaginal canal (950) in the fornix (910) and sits directly below the cervix (930). The dual durometer polymeric material menstrual disc-shaped device (100) is tucked behind the pubic bone (940) and uses the vaginal walls in the fornix (910) to create a seal. The dual durometer polymeric material menstrual disc-shaped device (100) differs from the menstrual cup (960) in that the user can use the dual durometer polymeric material menstrual disc-shaped device (100) during sexual intercourse to potentially block fluids from entering or exiting the uterus (920).

Figure 8:
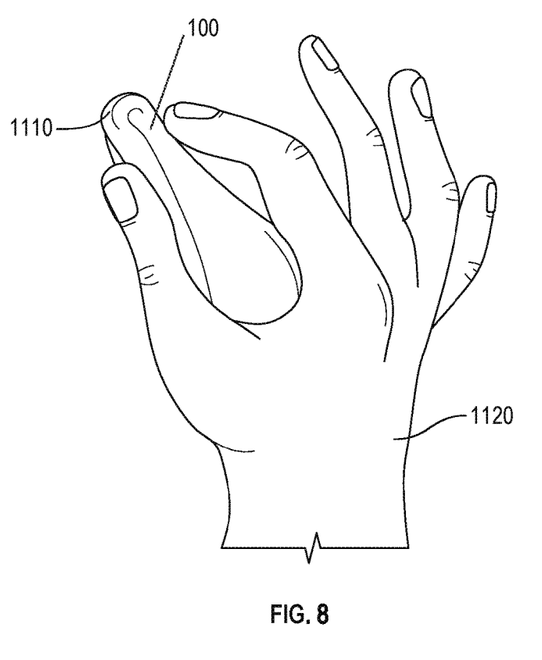
FIG. 8 illustrates one method of holding the menstrual disc shaped device folded in a teardrop shape prior to insertion.
Figure 9:
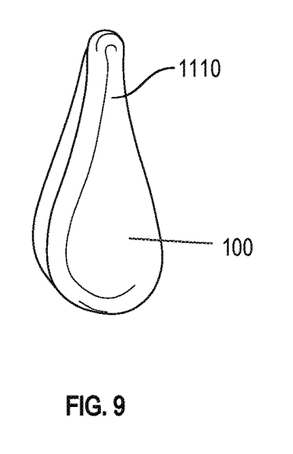
FIG. 9 illustrates one version of the menstrual disc shaped device with the tear drop shape.

As stated above, FIG. 8 illustrates one method of holding the menstrual disc shaped device folded in a teardrop shape prior to insertion, while FIG. 9 illustrates the tear drop shape of the menstrual disc shaped device.

FIG. 8 shows how the menstrual disc will be held in the hand (1120) while folded in the teardrop shape (1110). Here the dual durometer polymeric material menstrual disc-shaped device (100) is in the "pinched configuration". The user would then insert their fingers with the folded pinched configuration disc (1110) into their vagina and continue to push it in as far as possible until it reaches the fornix (910) of FIG. 6 and FIG. 7 and opens. The part of the rim that the user can reach with their finger gets tucked under the pubic bone (940) of FIG. 6 and FIG. 7. Once the dual durometer polymeric material menstrual disc-shaped device (100) of FIG. 7 is tucked under the pubic bone (940), it is in the proper preferred location.

FIG. 9 indicates what and how the dual durometer polymeric material menstrual disc-shaped devices (100) are folded into the teardrop shape (1110) prior to insertion. The pinched top of the menstrual discs (100) are folded and pinched into a teardrop shape (1110) that provides for the dual durometer polymeric material menstrual disc-shaped device (100) to achieve the smallest possible shape for easier and more comfortable insertion than has previously been possible. The teardrop shape for the menstrual discs folded in teardrop shape (1110) as shown differs from other FIG. 8 shaped alternate possible shapes that created much larger, more uncomfortable, and sometimes impossible shapes that could be used for insertion into the vaginal canal.

What is claimed is:

1. A reusable menstrual discharge collection device, comprising:
    a continuous single piece article that forms a disc-shaped menstrual discharge collection device with a half spherical dome catch such that said half spherical dome catch includes a continuous top and bottom portion, wherein said continuous top portion is attached to a uniform continuous flexible hinge that is placed along an entire circumferential upper portion of said half spherical dome catch and wherein said hinge also forms a base for and is connected to a 360-degree uniform continuous rim section such that said hinge allows said half spherical dome catch to be in an inverted use position that allows movement of said catch section toward said uniform continuous rim section such that said menstrual discharge collection device provides adjustability and ease of extraction with a required flexibility so that said menstrual discharge collection device fits multiple cervix physiologies and wherein said device is comprised of two separate polymers with different durometers such that said half spherical dome catch and said continuous flexible hinge are physically connected to an inside diameter of the said 360 degree uniform continuous rim in an elongated configuration.

2. The reusable menstrual discharge collection device of claim 1, wherein said device is formed as a single article that initially is from two separate portions from two separate mold cavities such that a first mold cavity provides said rim section with a Shore A hardness of no less than 45 and a second mold cavity provides said catch and said uniform continuous flexible hinge with a Shore A hardness of no greater than 35.

3. The reusable menstrual discharge collection device of claim 1, wherein said device includes an elongated configuration that provides for both ease of manufacturing and for cleaning said menstrual discharge collection device after use.

4. The reusable menstrual discharge collection device of claim 1, wherein said device is a menstrual disc-shaped device that functions as a shallow cup.

5. The reusable menstrual discharge collection device of claim 1, wherein said device is formed as a single article in a single mold that processes injection molded high temperature resistant thermoplastic rubber.

6. The reusable menstrual discharge collection device of claim 1, wherein said rim section of said discharge collection device has a Shore A hardness of at least 45.

7. The reusable menstrual discharge collection device of claim 1, wherein said half spherical dome catch is collapsible so as to be enclosed within said rim section when said device is in a use position.

8. The reusable menstrual discharge collection device of claim 1, wherein said rim section has rounded edges.

9. The reusable menstrual discharge collection device of claim 1, wherein said half spherical dome catch is collapsible so that said half spherical dome catch is enclosed within said rim section during use, and wherein said menstrual discharge device is foldable into a tear drop-like position that provides greater ease of insertion than conventional menstrual discharge collection devices.

10. The reusable menstrual discharge collection device of claim 8, wherein an absorbent and antimicrobial substance is infused into said half spherical dome catch and more precisely within a bottom portion of said half spherical dome catch, and wherein a distance between said bottom portion of said reservoir and said rim is no less than approximately thirty millimeters when said reservoir is in said device-shaped configuration.

11. The reusable menstrual discharge collection device of claim 9, wherein a pharmaceutical or other medically active substance is infused into said half spherical dome catch and more precisely within a bottom portion of said half spherical dome catch, and wherein a distance between said bottom portion of said reservoir and said rim is no less than approximately thirty millimeters when said reservoir is in said device-shaped configuration.

12. The reusable menstrual discharge collection device of claim 1, wherein said rim section is an elastomeric rim section that together with said half spherical dome catch defines a first generally circular configuration for creating a collection space for collecting menstrual discharge, said rim section being compressible from said first configuration to a second generally tear drop-shaped configuration for insertion of said menstrual discharge collection device into position for use, wherein diametrically opposed portions of said rim section are in contact with each other when said rim section is in said second configuration, and wherein said rim section is capable of self-restoring from said second configuration to said first configuration, and wherein said rim section has a height, and a thickness, and wherein said rim section is formed of a high temperature resistant injection molded thermoplastic rubber; and wherein said rim section is formed of liquid silicone rubber.

13. The reusable menstrual discharge collection device of claim 11, wherein said device is entirely formed with liquid silicone rubber.

14. A method of using a reusable menstrual discharge collection device, comprising:
    providing a continuous single piece article that forms a disc-shaped device with a half spherical dome catch, said half spherical dome catch includes a continuous top and bottom portion, wherein said continuous top portion is attached to a uniform continuous flexible hinge that is placed along an entire full and uniform circumferential upper portion of said half spherical dome catch and wherein said hinge also forms a base for and is connected to a 360 degree continuous uniform circumferential rim section such that said hinge allows half spherical dome catch to be in an inverted use position that allows movement of said catch section toward said continuous uniform rim section while providing movement and adjustability to fit multiple cervix configurations and an elongated configuration that allows ease of cleaning and manufacturing and;

said user is able to hold a folded teardrop-shaped configuration of said disc-shaped device and insert said device into their vagina and continue insertion in order to allow pushing said device until said device reaches a fornix of said user and such that a part of said 360 degree continuous rim section of said device is reachable with said user's finger(s) thereby allowing for tucking said device under a pubic bone of said user.

15. The method of claim 14, wherein once said menstrual discharge collection disc shaped device is tucked under said pubic bone said device is in a proper preferred location.

16. The method of claim 14, wherein said menstrual discharge collection disc shaped device is folded into a teardrop shape prior to insertion thereby providing a smallest possible shape for easier and more comfortable insertion than previous menstrual devices.

* * * * *